US00PP30956P2

(12) United States Plant Patent

Olesen et al.

(10) Patent No.: US PP30,956 P2
(45) Date of Patent: Oct. 22, 2019

(54) *CLEMATIS* PLANT NAMED 'EVIPO084'

(50) Latin Name: *Clematis viticella*
Varietal Denomination: Evipo084

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,907

(22) Filed: Sep. 10, 2018

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
CPC ..... A01H 5/02; A01H 6/72
See application file for complete search history.

(56) References Cited

PUBLICATIONS

PLUTO Plant Variety Database Apr. 11, 2019.*

* cited by examiner

*Primary Examiner* — Annette H Para

(57) ABSTRACT

A new *Clematis* plant with a compact growth habit, profuse, red flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo084'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo084' originated as a single seedling from the stated cross.

The new *Clematis* plant may be distinguished from its female seed parent and male pollen parent by the following characteristics. The female seed parent has an overall growth height of 150 cm, while the new variety grows less vigorous, to 60-80 cm. The male seed parent has Red 53A tepals while the new variety has Red-Purple Group 59A colored tepals.

The objective of the hybridization of this *Clematis* plant was to create a new and distinct variety for nursery culture with unique qualities such as:

1. Uniform and abundant red flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo084' was selected by Mogens N. Olesen and Raymond J. Evison in their *Clematis* development program in the Channel Islands, United Kingdom in 2006. Asexual reproduction of 'Evipo084' by means of vegetative cuttings and traditional layering was first performed by Mogens N. Olesen and Raymond J. Evison in the nursery during the summer of 2006. This initial and subsequent asexual propagations have demonstrated that the characteristics of 'Evipo084' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo084'.

Specifically illustrated in FIG. 1 of the drawings is an open flower, tepals detached showing reproductive flower parts, and flower buds.

Figure 1:
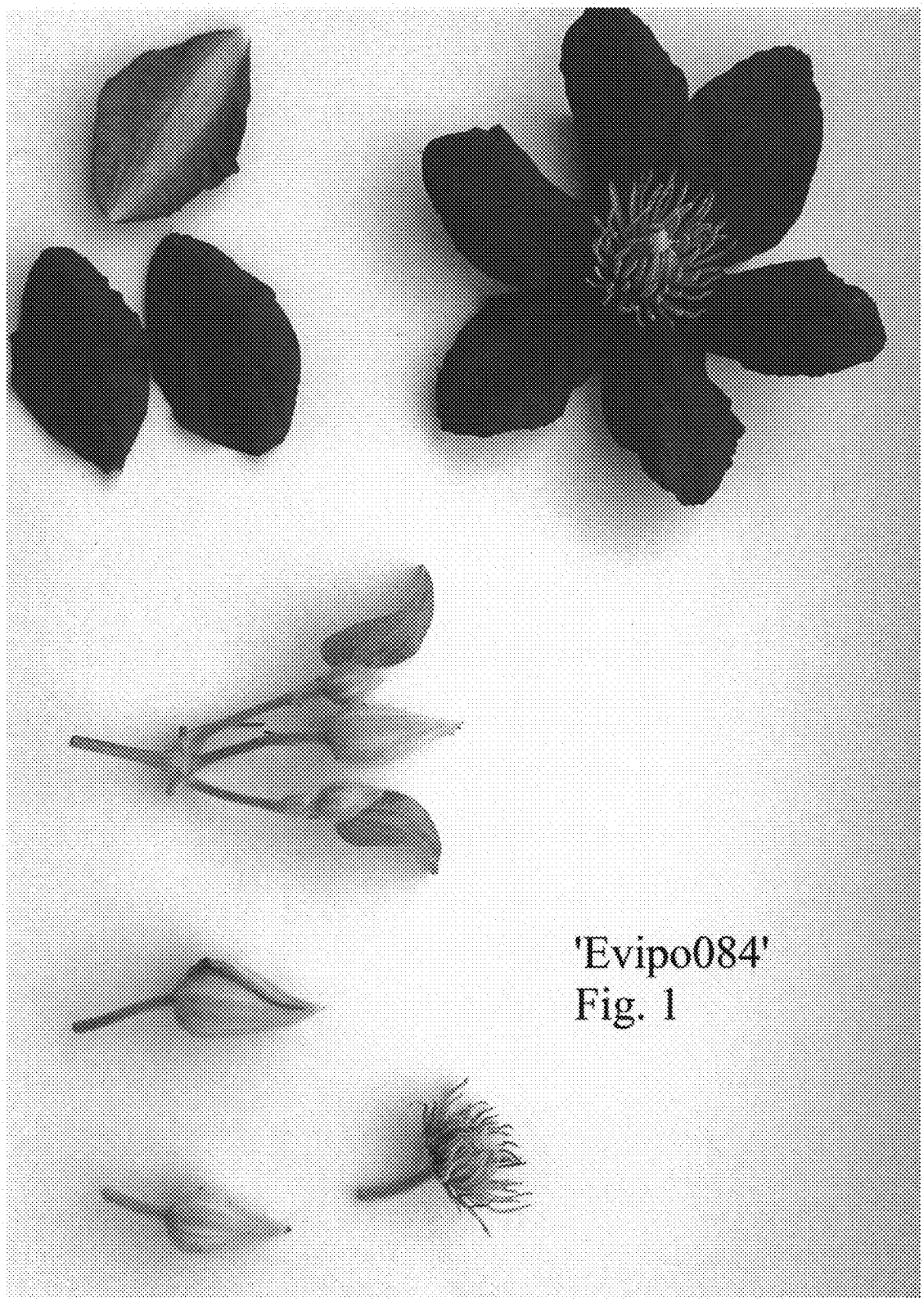
Figure 2:
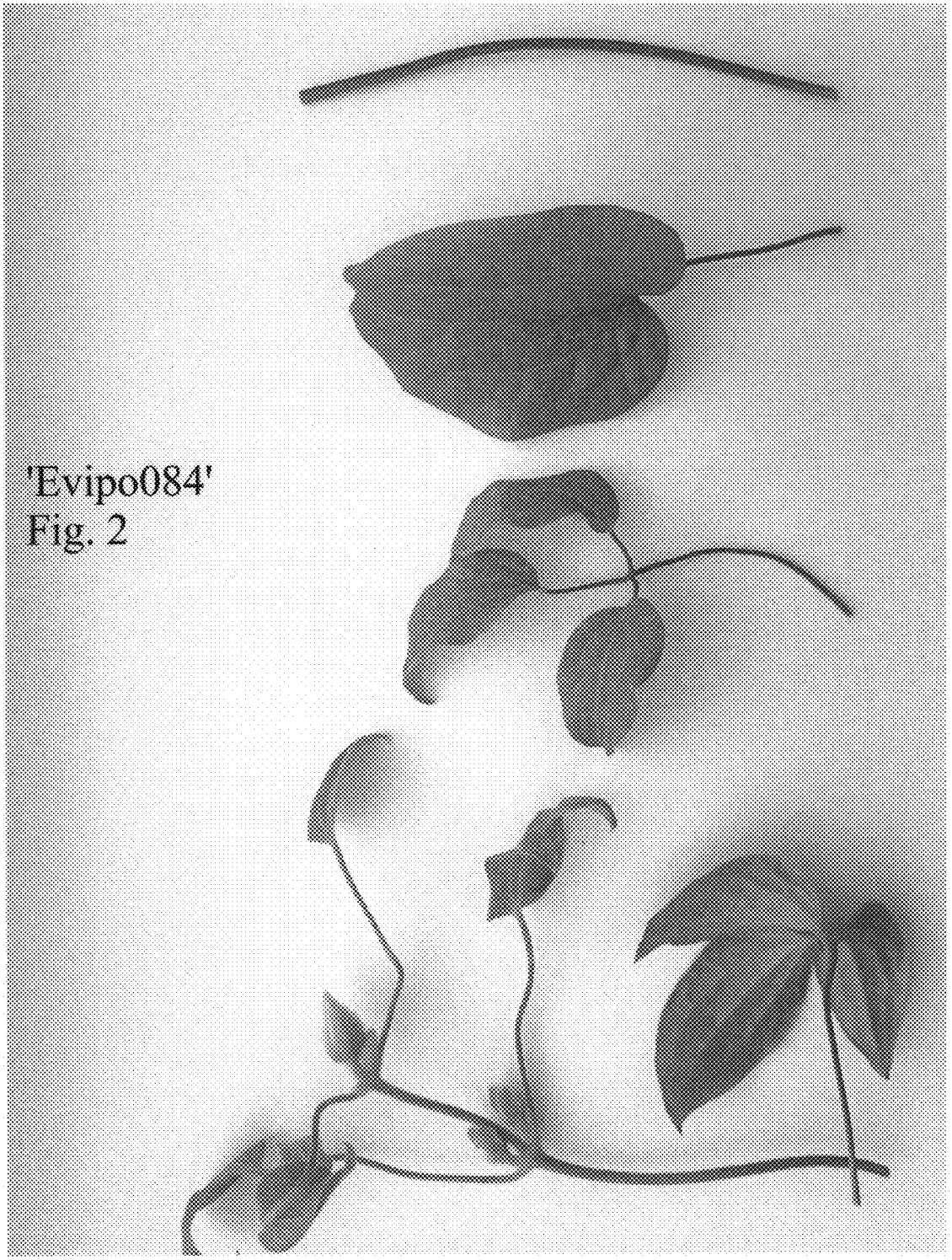
FIG. 2 shows leaves and stems.

Illustrated plants are 2 years of age.

DETAILED DESCRIPTION OF THE VARIETY

The following is a detailed description of 'Evipo084', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo069' described and illustrated in U.S. Plant Pat. No. 27,714 are compared to 'Evipo084' in Chart 1.

CHART 1

| | 'Evipo084' | 'Evipo069' |
|---|---|---|
| Growth height of the plant | 60 to 80 cm | 2 to 3 meters |
| Tepal upper surface after opening | Red-Purple Group 59A | Red-Purple Group 59A |
| Filament color | Violet Group 84A and 84B | Green-Yellow Group 1D |

FLOWER AND FLOWER BUD

Blooming habit: Recurrent. The natural flowering period is generally from April to September.

Flower bud:
- *Size*.—Normally 22 mm in length. Bud diameter is 13 mm.
- *Bud form*.—Elliptic.
- *Bud color*.—Yellow-Green Group 145B.
- *Texture*.—Pubescent.

Pedicel:
- *Surface texture*.—Smooth and lightly pubescent.
- *Length*.—On average 15-30 mm in length with 2 mm diameter.
- *Color*.—Yellow-Green Group 145B.
- *Strength*.—Moderately strong.

Receptacle:
- *Surface texture*.—Smooth and lightly pubescent.
- *Shape*.—Broad funnel.
- *Size*.—1 mm (h)×3 mm (w).
- *Color*.—Yellow-Green Group 145B.

Flower arrangement:
- *Location on vine*.—New growth only.
- *Borne*.—Normally in clusters of 3 flowers.

Flower bloom:
- *Size*.—On average, flowers are 100 mm in diameter and 20 mm in depth.
- *Profile*.—Open flowers are flat convex.
- *Fragrance*.—None.
- *Lasting quality*.—Flowers normally remain up to 10 days on the plant.

Tepals:
- *Tepal color*.—Upon opening, the upper surface is Red-Purple Group 59A. The lower surface upon opening is Red-Purple Group 59A with a stripe of Yellow-Green Group 145C. After opening, the upper surface is Red-Purple Group 59A. The lower surface after opening is Red-Purple Group 61A with a stripe of Yellow-Green Group 145D.
- *Quantity*.—Normally 6 tepals.
- *Size*.—45 mm in length by 30 mm wide.
- *Shape*.—Individual tepal shape is elliptic. The tepal apex is acute. The tepal base is rounded.
- *Apex recurvature*.—Slightly recurved.
- *Tepal overlap*.—Partial to none.
- *Tepal cross section*.—Reflexed.
- *Margins*.—Entire.
- *Persistence*.—Tepals drop off cleanly.

Reproductive organs:
- *Pollen*.—Quantity: Above average. Color: Yellow Group 2C.
- *Anthers*.—Size: 7 mm in length. Color: Greyed-Orange Group 177A. Quantity: On average, 80.
- *Filaments*.—Color: Violet Group 84A and 84B. Length: 10 mm.
- *Pistils*.—Quantity: On average, 35.
- *Stigmas*.—Superior in location relative to the length of the filaments and the height of the anthers. Color: Yellow Group 4C.
- *Styles*.—Color: Yellow Group 4C. Length: 15 mm.

Seed head characteristics: None observed.

PLANT

Plant form: Climbing.

Plant growth: Moderately vigorous.

Size: Seasons growth attains 60 to 80 cm in height. Average spread is 50 cm.

Stems:
- *Color*.—Juvenile stems are Greyed-Orange Group 166A and Yellow-Green Group 146B. Mature stems are Greyed-Purple Group 184A.
- *Internodes*.—On average, 12 cm between nodes.
- *Length*.—Normally 5 cm from the base of the plant to the flowering portion of the stem.
- *Diameter*.—About 2 - 3 mm.
- *Texture*.—Mature stems are smooth and lightly pubescent.

Plant foliage:
- *Leaf characteristics*.—Deciduous.
- *Arrangement*.—Mostly simple, some are ternate.
- *Leaf size*.—Simple leaves are 100 to 130 mm in length by 35 to 50 mm wide. Ternate, compound leaves are 100 to 130 mm in length by 80 to 120 mm wide.
- *Abundance*.—Usually 1 leaf per 10 cm of stem.
- *Leaf color*.—Juvenile upper Yellow-Green Group 144A. Juvenile lower Yellow-Green Group 144A. Mature upper Yellow-Green Group 144A. Mature lower Yellow-Green Group 146C.
- *Stipules*.—Absent.
- *Petioles*.—Size: 35 to 80 mm in length by 1 to 2 mm diameter. Texture: Smooth with light pubescence. Color: Greyed-Purple Group 183A.
- *Petioloule*.—Size: About 20 mm in length by 1 mm diameter. Texture: Smooth with light pubescence. Color: Greyed-Purple Group 183A.
- *Leaflet shape*.—Elliptic. The base is rounded and oblique. The apex is acute.
- *Margin*.—Entire.
- *Surface*.—The upper side is smooth, the lower side is smooth.
- *Thickness*.—Moderate.
- *Glossiness*.—Not glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo084', substantially as described and illustrated, due to its abundant red flowers with good keepability, attractive long lasting foliage and compact growth, suitability for production from softwood cuttings in pots, durable flowers and foliage which make the variety suitable for distribution in the floral industry.

* * * * *

'Evipo084'

'Evipo084'